United States Patent
Rothschild et al.

(10) Patent No.: US 7,551,715 B2
(45) Date of Patent: Jun. 23, 2009

(54) X-RAY INSPECTION BASED ON SCATTER DETECTION

(75) Inventors: Peter Rothschild, Boston, MA (US);
Jeffrey Schubert, Somerville, MA (US);
William J. Baukus, Nashua, NH (US);
William Wade Sapp, Jr., Melrose, MA (US); Richard Schueller, Chelmsford, MA (US); Joseph Callerame, Waltham, MA (US); William Randall Cason, Tewksbury, MA (US)

(73) Assignee: American Science and Engineering, Inc., Billerica, MA (US)

( * ) Notice: Subject to any disclaimer, the term of this patent is extended or adjusted under 35 U.S.C. 154(b) by 123 days.

(21) Appl. No.: 11/551,991

(22) Filed: Oct. 23, 2006

(65) Prior Publication Data
US 2007/0098142 A1      May 3, 2007

Related U.S. Application Data

(60) Provisional application No. 60/748,909, filed on Dec. 9, 2005, provisional application No. 60/729,528, filed on Oct. 24, 2005, provisional application No. 60/729,548, filed on Oct. 24, 2005.

(51) Int. Cl.
*G01N 23/04* (2006.01)
(52) U.S. Cl. .......................... 378/57; 378/198
(58) Field of Classification Search .............. 378/57, 378/51, 62, 70, 86, 88, 145, 146, 160, 193–198
See application file for complete search history.

(56) References Cited

U.S. PATENT DOCUMENTS

| | | | |
|---|---|---|---|
| 3,569,708 A | 3/1971 | Weinbaum et al. | 250/83.3 |
| 3,868,506 A | 2/1975 | Osigo | 250/278 |
| RE28,544 E | 9/1975 | Stein et al. | 250/369 |
| 3,928,765 A | 12/1975 | Teller | 250/272 |
| 4,047,029 A | 9/1977 | Allport | 250/273 |
| 4,052,617 A | 10/1977 | Garrett et al. | 250/360 |
| 4,260,898 A | 4/1981 | Annis | 378/146 |
| 4,342,914 A | 8/1982 | Bjorkholm | 378/99 |
| 4,458,152 A | 7/1984 | Bonora | 250/353 |
| 4,472,822 A | 9/1984 | Swift | 378/10 |
| 4,768,214 A | 8/1988 | Bjorkholm | 378/87 |
| 4,799,247 A | 1/1989 | Annis et al. | 378/87 |
| 4,809,312 A | 2/1989 | Annis | 378/146 |
| 4,839,913 A | 6/1989 | Annis et al. | |
| 4,864,142 A | 9/1989 | Gomberg | 250/390.04 |
| 4,884,289 A | 11/1989 | Glockmann et al. | 378/57 |

(Continued)

FOREIGN PATENT DOCUMENTS

GB      2277013      10/1994

(Continued)

*Primary Examiner*—Courtney Thomas
(74) *Attorney, Agent, or Firm*—Bromberg & Sunstein LLP

(57) ABSTRACT

Systems and methods for inspecting an object with a scanned beam of penetrating radiation are disclosed. Scattered radiation from the beam is detected, in either the backward or forward direction. Characteristic values of the backscattered radiation are compared to expected reference values to characterize the object. Additionally, penetrating radiation transmitted through the inspected object may be combined with scatter information. In certain embodiments, the inspected field of view is less than 0.1 steradians, and the detector is separate from the source of penetrating radiation and is disposed, with respect to the object, such as to subtend greater than 0.5 steradians in the field of view of the object.

18 Claims, 16 Drawing Sheets

U.S. PATENT DOCUMENTS

| | | | |
|---|---|---|---|
| 4,899,283 A | 2/1990 | Annis | 378/7 |
| 4,974,247 A | 11/1990 | Friddell | 378/90 |
| 5,002,397 A | 3/1991 | Ingrum et al. | 356/407 |
| 5,014,293 A | 5/1991 | Boyd et al. | 378/197 |
| 5,022,062 A | 6/1991 | Annis | 378/86 |
| 5,065,418 A | 11/1991 | Bermbach et al. | 378/57 |
| 5,068,883 A | 11/1991 | DeHaan et al. | |
| 5,091,924 A | 2/1992 | Bermbach et al. | 378/57 |
| 5,132,995 A | 7/1992 | Stein | 378/56 |
| 5,164,976 A | 11/1992 | Scheid et al. | 378/146 |
| 5,179,581 A | 1/1993 | Annis | 378/57 |
| 5,181,234 A | 1/1993 | Smith | 378/87 |
| 5,224,144 A | 6/1993 | Annis | 378/144 |
| 5,247,561 A | 9/1993 | Kotowski | 378/87 |
| 5,253,283 A | 10/1993 | Annis et al. | 378/100 |
| 5,302,817 A | 4/1994 | Yokota et al. | 250/214 |
| 5,313,511 A | 5/1994 | Annis et al. | 378/87 |
| 5,479,023 A | 12/1995 | Bartle | 250/390.04 |
| 5,591,462 A | 1/1997 | Darling et al. | 425/173 |
| 5,629,966 A | 5/1997 | Dykster et al. | 378/57 |
| 5,638,420 A | 6/1997 | Armistead | 378/57 |
| 5,692,028 A | 11/1997 | Geus et al. | 378/57 |
| 5,692,029 A | 11/1997 | Husseiny et al. | 378/88 |
| 5,764,683 A * | 6/1998 | Swift et al. | 378/57 |
| 5,838,759 A | 11/1998 | Armistead | 378/57 |
| 5,903,623 A | 5/1999 | Swift et al. | 378/57 |
| 6,067,344 A | 5/2000 | Grodzins et al. | 378/117 |
| 6,094,472 A | 7/2000 | Smith | 378/86 |
| 6,124,647 A | 9/2000 | Marcus et al. | 307/10.1 |
| 6,151,381 A | 11/2000 | Grodzins et al. | 378/90 |
| 6,203,846 B1 | 3/2001 | Ellingson | |
| 6,249,567 B1 | 6/2001 | Rothschild et al. | 378/88 |
| 6,252,929 B1 | 6/2001 | Swift et al. | 378/57 |
| 6,269,142 B1 | 7/2001 | Smith | 378/57 |
| 6,278,115 B1 | 8/2001 | Annis et al. | |
| 6,282,260 B1 * | 8/2001 | Grodzins | 378/87 |
| 6,292,533 B1 | 9/2001 | Swift et al. | 378/57 |
| 6,356,620 B1 | 3/2002 | Rothschild et al. | 378/160 |
| 6,424,695 B1 | 7/2002 | Grodzins et al. | 378/87 |
| 6,434,219 B1 | 8/2002 | Rothschild et al. | 378/160 |
| 6,658,087 B2 | 12/2003 | Chalmers et al. | 378/86 |
| 6,727,506 B2 | 4/2004 | Mallette | 250/394 |
| 7,010,094 B2 | 3/2006 | Grodzins et al. | 378/86 |
| 2002/0097836 A1 | 7/2002 | Grodzins et al. | 378/57 |
| 2003/0016790 A1 | 1/2003 | Grodzins et al. | 378/147 |
| 2003/0091145 A1 | 5/2003 | Mohr et al. | 378/58 |
| 2004/0086078 A1 | 5/2004 | Adams et al. | |
| 2004/0251415 A1 | 12/2004 | Verbinski | |

FOREIGN PATENT DOCUMENTS

| | | |
|---|---|---|
| GB | 2287163 | 9/1995 |
| GB | 2400480 | 10/2004 |
| JP | 63079042 | 4/1988 |
| WO | WO 00/33060 | 6/2000 |
| WO | WO 0037928 | 6/2000 |
| WO | WO 2004/043740 | 5/2004 |

* cited by examiner

X-RAY INSPECTION BASED ON SCATTER DETECTION

The present application claims priority from three U.S. Provisional Patent Applications, Ser. Nos. 60/729,528 (filed Oct. 24, 2005), 60/729,548 (filed Oct. 24, 2005), and 60/748,909 (filed Dec. 9, 2005), all three of which applications are incorporated herein by reference.

FIELD OF THE INVENTION

The invention generally relates to inspection systems based upon remote detection of penetrating radiation scattered by an inspected object.

BACKGROUND ART

X-ray scattering may be employed for inspection of personnel, vehicles, cargo, or other objects of interest. The term "object" is used inclusively herein to encompass any of the above. In systems employing x-ray scattering, x-rays are formed into a beam that is directed towards the object of interest. When the beam hits the object, scattered X-rays are captured by x-ray detectors and various characteristics of the scattering object may be ascertained, either globally, or with respect to a pixelated image of the object.

The resolution of information obtained about the interrogated object or person is dependent upon a variety of factors including the distance between the inspection system and the object, and the magnitude and energy spectrum of the x-ray flux. In current systems, as the distance between the X-ray system and the object increases or as the flux decreases, the image resolution and quality (as manifest in the signal-to-noise, for example) decreases. The decrease in quality is substantially caused by the reduction of backscattered flux captured by the detectors. Current backscatter x-ray imaging systems locate detectors adjacent to the x-ray source, allowing the combined system of source and detectors to be as close as possible to the object being inspected. The proximity of the system to the object creates a high quality image without the need for a high x-ray flux.

However, there are many applications, especially security and surveillance applications, where a larger distance between the imaging system and the object to be inspected would be desirable. One such application is where personnel to be inspected might be carrying explosive devices carried under clothing or concealed in backpacks or bags and the risk of suicide detonation is present. Suicide bombings have often entailed large quantities of metal shrapnel packed around the explosive to maximize the lethality of the device, typically nuts, nails, or ball-bearings.

Current x-ray inspection systems are often inadequate in such applications and are rarely used in applications requiring distances greater than five feet. Current systems can counteract the decrease in image quality by increasing the size of the detectors or using higher flux x-ray sources. However, if the distances are too great, the detectors required will be impractically large. Additionally, as the flux increases, so will the objects exposure, which poses a problem when the object is, or may contain, a person.

One scenario for backscatter inspection from a mobile inspection vehicle is described in U.S. Pat. No. 7,099,434, to Adams et al., issued Aug. 29, 2006 and incorporated herein by reference. Embodiments of that invention can be highly effective at detecting large quantities of explosives or other organic materials in vehicles or other containers. One consideration, however, is that metal objects (such as artillery shells) within a metallic container (such as a vehicle) may not be well-detected unless favorably silhouetted against a brightly scattering background of organic material.

Another issue for backscatter technology is that it can sometimes be difficult to image organic materials when they are placed within or behind significant amounts of high-Z material, such as steel. An example of this might be a small quantity of explosive concealed in the trunk of a vehicle. Because the backscattered x-rays are typically detected in the backward direction (scatter angles typically in the range $140°<\Theta<180°$), the average energy of the scattered x-rays is quite low (about 68 keV for a primary x-ray beam from a 225 kV x-ray source). These low-energy x-rays are then greatly attenuated by the steel body of the vehicle, resulting in a greatly reduced number of scattered x-rays being detected in the backscatter detectors. This problem is often exacerbated because the scattered x-rays reach backscatter detectors having passed through an intervening steel surface at an oblique angle, resulting in an effective thickness of steel that is greater than the actual gauge of the steel.

SUMMARY OF THE INVENTION

Representative embodiments of the present invention include a system and a method for inspecting an object. The object is illuminated with a collimated beam of penetrating radiation. Backscattered radiation from the beam is detected. Characteristic values of the backscattered radiation are compared to expected reference values. Based on the comparing, a descriptive category is determined which characterizes the object.

In further embodiments, the penetrating radiation may be x-ray radiation. The descriptive category may, for example, indicate abnormally high metallic content when the characteristic values are less than the expected reference values, or abnormally high organic content when the characteristic values are greater than the expected reference values. The descriptive category may indicate a potential or confirmed security threat according to pre-established security threat criteria.

In some embodiments, the method may further include selecting the object for illumination. This may be based, for example, on optical or non-optical surveillance of an area of interest. The method may also include determining the expected reference values based on illuminating a reference object with the penetrating radiation.

Embodiments of the present invention also include systems and devices adapted to employ any of the foregoing methods.

In accordance with another aspect of the present invention, a system and method are provided for inspecting an object of inspection with penetrating radiation. A beam of penetrating radiation is generated by a concealed source and scanned across the object with a time-variable beam direction. The penetrating radiation scattered by the object into a concealed transmission detector is detected, and a direct transmission signal is generated. A specified characteristic of the contents of the object is ascertained based in part on the direct transmission signal.

In a further embodiment, the transmission detector includes one or more linear sections, for example, an L-shaped detector having a vertical section and a horizontal section. And the transmission detector may be incorporated into a speed bump structure.

Another representative embodiment of the present invention includes a system and method for inspecting an object of inspection with penetrating radiation, again formed into a beam that is scanned across the object with a time-variable beam direction. The penetrating radiation scattered by the object into a forward scatter detector is detected, and a forward scatter signal is generated. A specified characteristic of the contents of the object is ascertained based in part on the forward scatter signal.

Further embodiments include combining a direct transmission detector and a forward scattering detector in a single system. In such an arrangement, the direct transmission signal and the forward scatter signal are combined to create an enhanced scatter image and/or an enhanced transmission image. Any of the images produced may be displayed to an operator. Any or all of the detectors may be incorporated into a speed bump structure.

Embodiments also include an improved inspection system of the type using an enclosure in which are concealed a source of penetrating radiation having a beam that is scannable along at least a first plane and a detector that is responsive to back scattered energy of the beam from an object being inspected. The improvement includes a transmission detector module for detecting radiation energy that has been transmitted through the object being inspected, such module being physically separated from the enclosure and deployable on a road.

Further embodiments include an improved inspection system of the type using an enclosure in which are concealed a source of penetrating radiation having a beam that is scannable along at least a first plane and a detector that is responsive to back scattered energy of the beam from an object being inspected. The improvement includes a forward scatter detector module for detecting radiation energy that has been scattered in a forward direction by the object being inspected, such module being physically separated from the enclosure and deployable on a road.

Embodiments also include an improved inspection system of the type using an enclosure in which are concealed a source of penetrating radiation having a beam that is scannable along at least a first plane and a detector that is responsive to back scattered energy of the beam from an object being inspected. The improvement includes a ramp module housing (i) a horizontal portion of a transmission detector module for detecting radiation energy that has been transmitted through the object being inspected and (ii) at least one forward scatter detector for detecting radiation energy that has been scattered in a forward direction by the object being inspected, such module being physically separated from the enclosure and deployable on a road.

In any of the above, the enclosure may form the outside of a vehicle capable of highway travel. Or the enclosure may be a ruggedized shipping container.

In accordance with other preferred embodiments of the present invention, an inspection system is provided for inspecting an object, the inspection system having a source of penetrating radiation disposed and configured such that the inspected field of view is less than 0.1 steradians (sr). A spatial modulator forms the penetrating radiation into a beam for irradiating the object being inspected. A detector is provided, separate from the source of penetrating radiation, disposed, with respect to the object, such as to subtend greater than 0.5 sr in the field of view of the object.

In various embodiments, the source of penetrating radiation may be an X-ray tube. Alternatively, the source of radiation may be a gamma ray beam. The spatial modulator may include one or more rotating chopper wheels.

In accordance with one embodiment of the present invention, the source of penetrating radiation may be placed at the center of a room and a number of portable detectors placed near the walls of the room. Alternatively, the source of penetrating radiation may be placed in an adjacent room and the detectors built into the walls of the room or located in adjacent rooms.

In accordance with further embodiments of the present invention, the source of penetrating radiation, the detector, or both may be located on one or more vehicles, including robotic drone vehicles, capable of road travel. The source of penetrating radiation may be mounted on a swivel mount to allow the beam to be directed at objects in various locations. The inspection system may further include a stabilization system to minimize bounce when the vehicle is traversing rough terrain.

In yet further embodiments of the present invention, the detectors may be located in the ground or ceiling of a passageway and may be camouflaged. Detectors located in the ground may further include structural supports to prevent damage to the detector when objects pass over, and pressure sensors to detect the presence of an object.

BRIEF DESCRIPTION OF THE DRAWINGS

The foregoing features of the invention will be more readily understood by reference to the following detailed description, taken with reference to the accompanying drawings, enumerated hereunder.

DETAILED DESCRIPTION OF SPECIFIC EMBODIMENTS

Distant Detection of Backscatter

Figure 1:
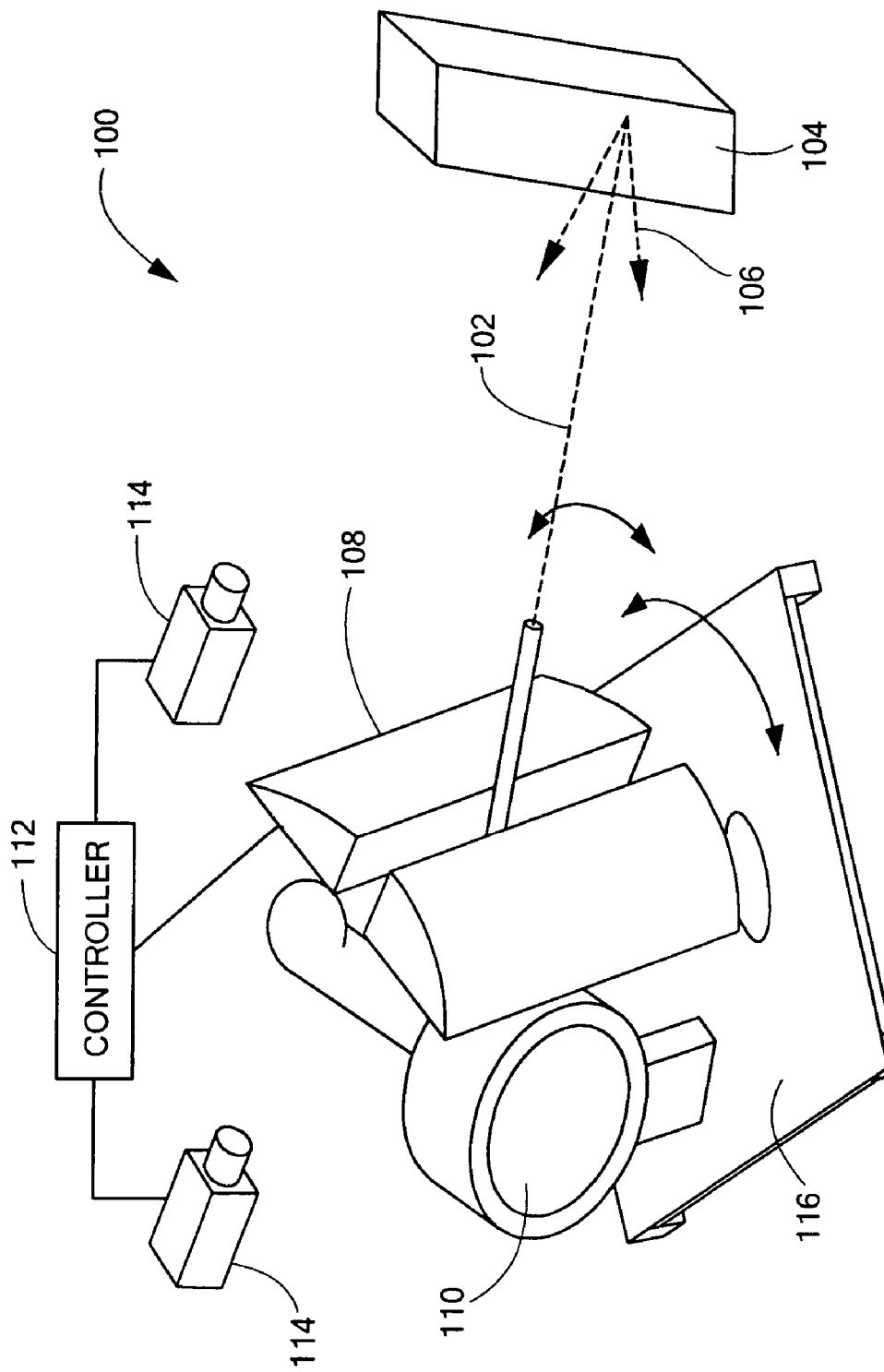
FIG. 1 shows various functional components according to a specific embodiment of the present invention.

Embodiments of the present invention (which may be referred to as "Z-Radar"™) are now described with reference to FIG. 1. A backscatter inspection system, designated generally by numeral 100, use a collimated beam 102 of penetrating radiation, such as x-rays, to illuminate an object 104 (which, as indicated above, may include a person) at relatively large distances, to determine, for example, the metallic content on or within the object. An object will be said to be disposed at a "large distance" if the object of inspection, or a relevant portion thereof, subtends an angle of less than 5° in any direction as viewed from the source of illumination. Penetrating radiation may also include, for example, waves in other portions of the electromagnetic spectrum, such as gamma rays, but will be referred to, herein, as x-rays, without intended loss of generality. When the penetrating radiation is comprised of x-rays, the x-rays may be generated by an x-ray source such as x-ray tube 110.

Penetrating radiation 106 scattered by the inspected object is detected in large-area x-ray detectors 108, and the signal generated by detectors 108 is compared, by controller 112, with the expected signal from organic objects illuminated with x-rays at that distance. Objects containing metals absorb the x-rays, resulting in a backscatter signal which is lower than the signal expected from a purely organic object.

Inspected objects can include without limitation people or any object which consists mostly of organic material, on or within which a determination of the metallic content is desired. For example, the metallic shrapnel used by a suicide bomber to maximize the lethality of the explosive being carried may be detected, or the presence of metallic weapons, such as guns and knives may be detected.

In some embodiments, the object to be examined is initially located and tracked with a system utilizing one or more video cameras 114, although any other optical or non-optical means may also be employed, within the scope of the invention. FIG. 1 shows various functional components according to one specific embodiment of the present invention. Video cameras 114 of an optical surveillance system monitor an area of interest. A steerable x-ray source 110 is mounted on a base 116 which can rotate and translate the position of a penetrating x-ray beam generated by x-ray tube 110. Backscatter detectors 108 detect the backscattered x-rays 106 from the target object 104 being illuminated. The video tracking system may be used to point the x-ray beam onto the object of interest. A shutter (not shown) can then be opened to allow the x-rays to briefly illuminate the target object for a pre-determined time period (known as the interrogation time). A data acquisition system records the intensity of a signal received from the backscatter detectors.

Figure 2:
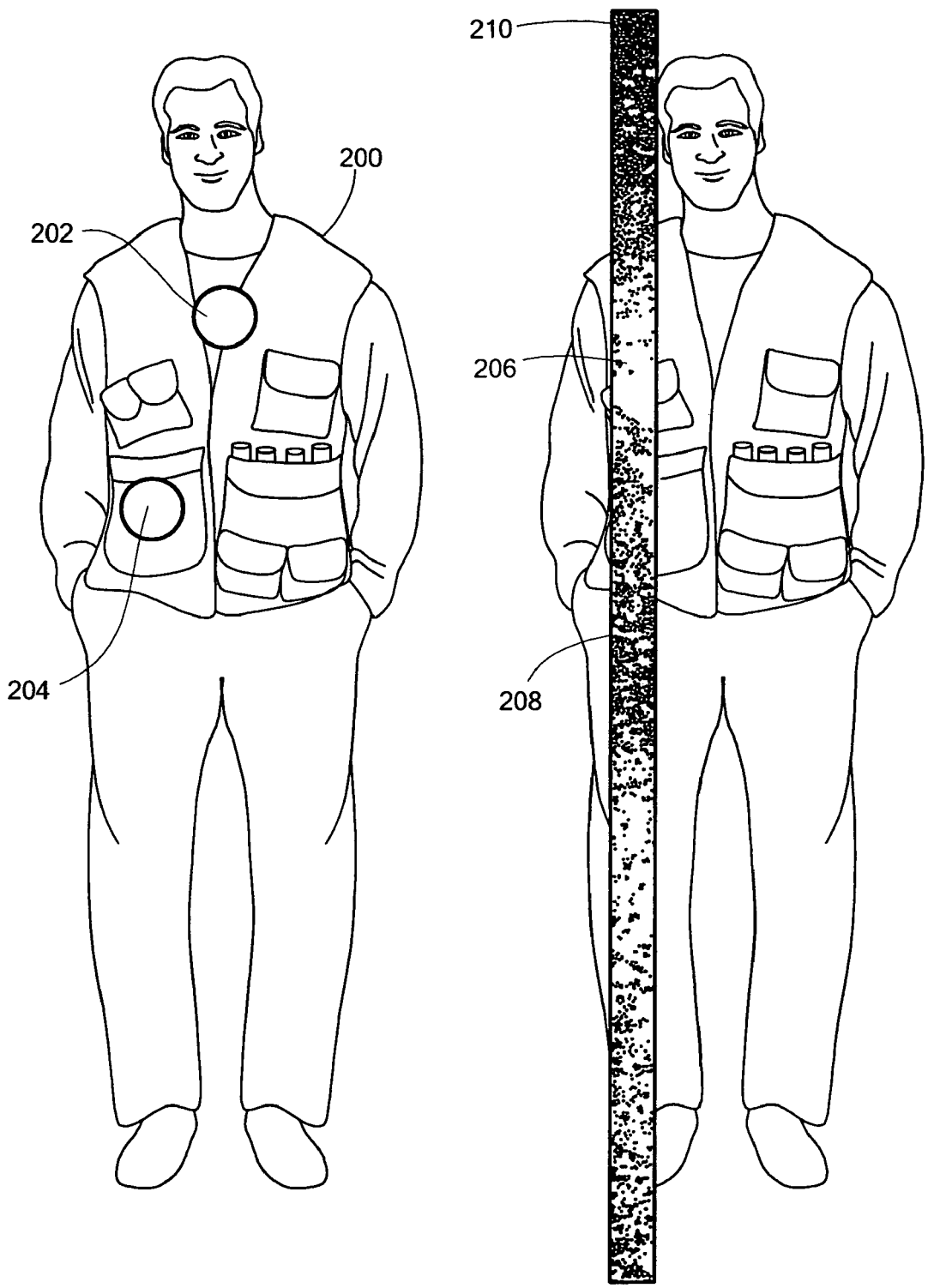
FIGS. 2A and 2B show aspects of various signal calibration schemes as used in specific embodiments.

Referring now to FIG. 2, in order to accurately calibrate the backscatter signal intensity, several illumination points (or "interrogation" points) 202, 204 can be chosen on the target 200, or on similar targets at the same distance. If the signal from one or more interrogation points appears significantly lower than that from the other interrogation points, it can be used to indicate the presence of metallic materials. On that basis, in accordance with embodiments of the invention, a descriptive category is determined, such as that of a heightened security threat according to pre-established security threat criteria, and appropriate action can then be taken accordingly.

Embodiments may also be suitable for determining the presence of organic materials on or within objects which largely consist of metallic materials. An example of this could be looking for explosives concealed in the door of a vehicle. For this application, interrogation points with a higher than expected signal are indicative of the presence of concealed organic material.

For objects which are relatively close to the x-ray source, the backscatter signal can also be used to detect the presence of dense organic material (such as explosives) concealed on an organic target object with a lower density. These materials tend to backscatter x-rays somewhat more strongly than less dense organic materials, such as the human body.

In Table 1, the results of a computer simulation are shown for an x-ray backscatter interrogation system operating at three source voltages of 160 kV, 450 kV, and 1.2 MeV. The simulations involved looking at the backscatter signal from a person at various distances, and comparing the signal with the signal from a person carrying a steel sheet or a person carrying PETN explosive containing ball-bearings as shrapnel. The signal to noise ratio (SNR) is defined by:

$$SNR = \frac{N_{Person} - N_{Person+Steel}}{\sqrt{N_{Person}}}$$

where $N_{Person}$ is the number of detected backscattered x-rays from a person carrying no steel and $N_{Person+Steel}$ is the number of detected backscattered x-rays from a person carrying steel. It can be seen that the performance of the 225 kV and 450 kV systems is essentially the same, but considerably better than the performance of the 1.2 MV system. Since a 160 kV system would be much cheaper and more compact than a 450 kV system, a preferred source voltage is about 160 kV. The following Table indicates the results of a computer simulation showing the signal-to-noise ratio for detecting metal on a person (in the form of a steel sheet or a matrix of 0.25" ball-bearings) with an x-ray backscatter interrogation system operating at three different source voltages and various standoff distances.

| Source Voltage | Standoff Distance (feet) | SNR (Steel) | SNR (Ball Bearings) |
|---|---|---|---|
| 160 kV | 50 | 77.2 | 47.5 |
| | 100 | 11.5 | 9.8 |
| | 150 | 3.3 | 2.7 |
| 450 kV | 100 | 11.1 | 9.9 |
| 1.2 MV | 100 | 4.4 | 4.5 |

Calibration of the Backscatter Signal

As discussed above, some embodiments employ techniques for calibrating the strength of the detected backscatter signal with a reference signal in order to determine whether the signal from an interrogation point is low enough to signify the presence of metal. This can be done in a number of ways:

1. Determine the distance to the target object being interrogated (for example, by using information from the video system or using a laser range finder) and use lookup tables to determine the maximum backscatter signal for metallic material. One disadvantage of this approach is that the system hardware should be relatively stable.
2. Compare the signal strength from a number of interrogation points from objects all at approximately the same distance.
3. Compare the signal strength from a number of interrogation points 202, 204 from different locations on the same object. This approach is shown schematically in the FIG. 2A.
4. Acquire a line scan 210 (shown in FIG. 2B) consisting of many interrogation points across the object, and look for regions 208 on the object where the backscatter brightness is significantly lower than for the rest of the object 206. This approach is shown schematically in FIG. 2B.

Figure 3:
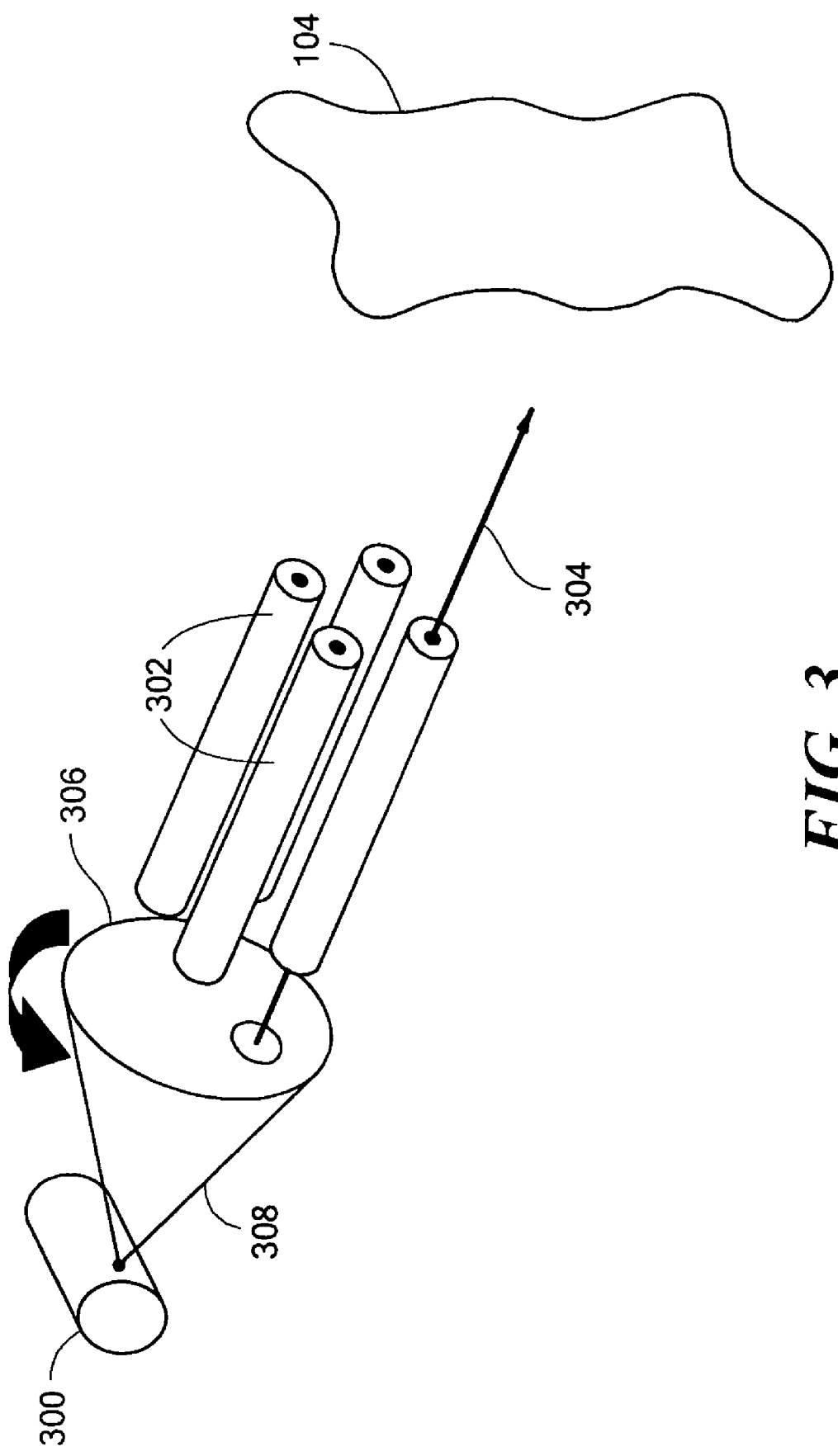
FIG. 3 shows details of an embodiment in which several interrogation points are rapidly established.

One method for simultaneously acquiring interrogation data and obtaining a reference signal is illustrated in FIG. 3. In this embodiment, the collimation scheme, such as multiple collimators 302 allows for several highly-collimated x-ray beams 304 to be produced simultaneously. A rotating shutter 306, disposed within x-ray cone beam 308 produced by x-ray source 300, is then used to ensure that at any instant only one of the beams is actually illuminating the target object 104. For the example shown in FIG. 3, this means that four interrogation points can be acquired in the time that it takes the shutter to rotate through one revolution. One advantage of this embodiment is that the speed of operation of the system can be enhanced, as the beam collimators do not physically have to be re-directed between interrogation points. The system may only have to be targeted once onto the central region of a suspicious object. The number of beams and their orientation with respect to each other can be optimized for the particular target objects being inspected.

One specific embodiment of the present invention operates as follows:

1. An operator identifies a suspicious target which he wishes to interrogate with the system. This could be done, for example, by clicking a mouse on the suspicious object in a video image. The operator may wish to identify, for example, a person wearing bulky clothing or carrying a backpack.
2. The interrogation system then sends out a pulse of x-rays in a highly-collimated beam, directed at the target object. By comparing the return backscatter signal with a reference signal (using one of the calibration methods discussed above), the system automatically determines the threat level of the object.
3. The system then alerts the operator, who can then determine what further action needs to be taken. If the threat determination is deemed to be uncertain, the system could continue to track the suspicious target using a video tracking system, and could perform a further confirming interrogation (if required) at a closer distance.
4. For confirmed threats (targets with substantial metallic content), the system may then initiate further inspection using additional systems that employ other inspection or detection modalities, such as x-ray backscatter imaging, mm-wave imaging, or terra-Hertz spectroscopy. These may be used to confirm the presence of weapons or explosives on or within the target object.

Forward Scatter Detection in Backscatter Inspection Scenarios

Detection, using illumination by penetrating radiation, either from a mobile platform such as the Mobile Inspection Van described in U.S. Pat. No. 7,099,434, or from a fixed platform such as the Ruggedized Detection Imaging Module™ (RDIM), may be enhanced with respect to the detection of metal objects, such as might be concealed, for example, within a metal container. Embodiments of the present invention offer improved detection of a metal object within a metal container by adding a stationary transmission detector on the other side of the object being scanned with a pencil beam, where the source of the pencil beam, and either backscatter, forward scatter, or transmission detectors are concealed from view from the vantage of the inspected object.

Figure 4:
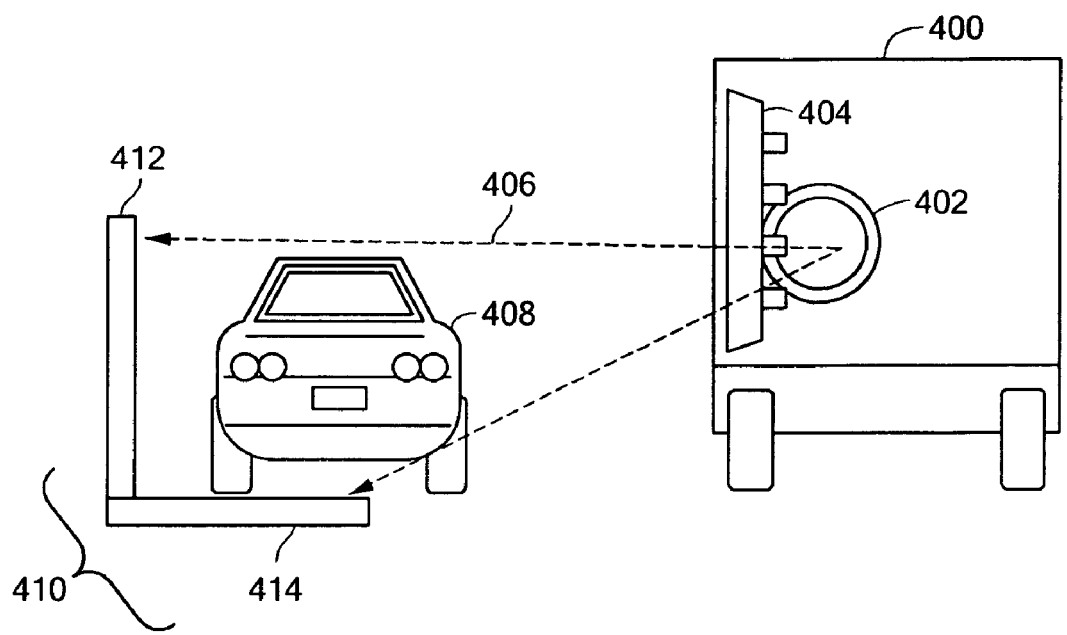
FIG. 4 shows a transmission detector placed at the far side of a vehicle being imaged according to one embodiment of the present invention.

Thick metallic materials disposed can be clearly seen in the transmission image, derived as shown in FIG. 4, where attenuated, or blocked, transmission is due to the high attenuation of x-rays in these materials. As used herein, the term "metallic" is a proxy for materials of high "Z", where Z represents the atomic number characteristic of the material. For example, artillery shells will appear as very dark objects in the transmission image, with little or no x-rays penetrating through them. Note that this can be done when the Mobile Inspection Van 400 is operated either in motion or in the stationary portal mode. FIG. 4 depicts source 402 and backscatter detector module 404 disposed within Mobile Inspection Van 400, and x-ray beam 406 scanning object 408. Transmission detection module 410 is here comprised of an upright vertical segment 412 and a horizontal segment 414.

Figure 5:
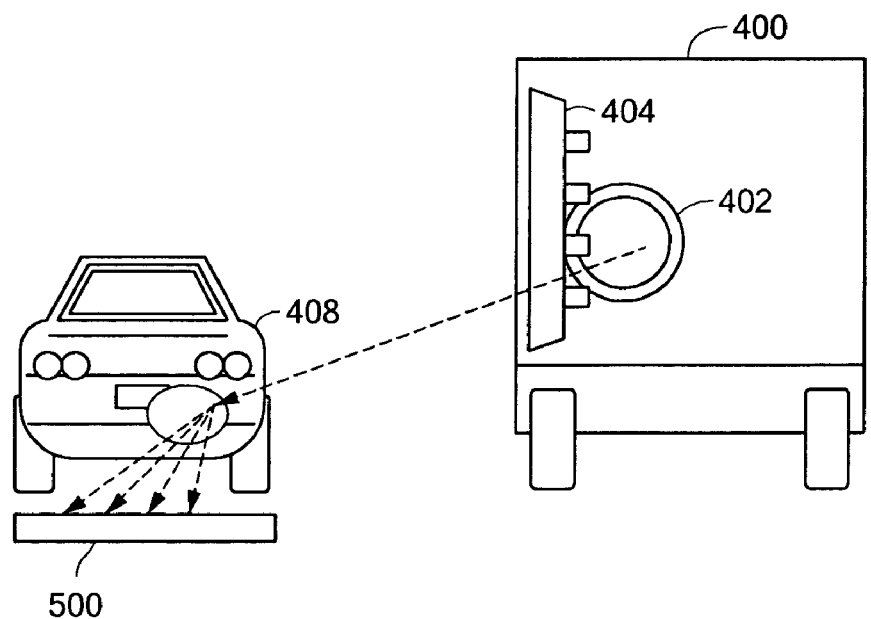
FIG. 5 shows a forward scatter detector placed underneath a vehicle for imaging according to one embodiment of the present invention.

One way to help mitigate the problem of imaging organic materials within or behind significant amounts of high-Z material (such as metal) is to add some forward-scatter detectors 500 as shown in FIG. 5. Because the forward-scattered x-rays 510 detected in these detectors have only been scattered through small angles (typically in the range of scattering angles, $5°<\Theta<30°$), the average energy of the forward-scattered x-rays is significantly higher than the energies of back-scattered x-rays (which are typically no greater than about 90 keV for a primary x-ray beam from a 225 kV x-ray source). This is due to conservation of momentum in the Compton scattering process. The higher energy of forward-scattered x-rays allows them to more easily penetrate the steel in the vehicle body and be detected. The signal from the forward-scatter detectors can either be combined with the backscatter signal, or it can be displayed separately to the operator.

Figure 6:
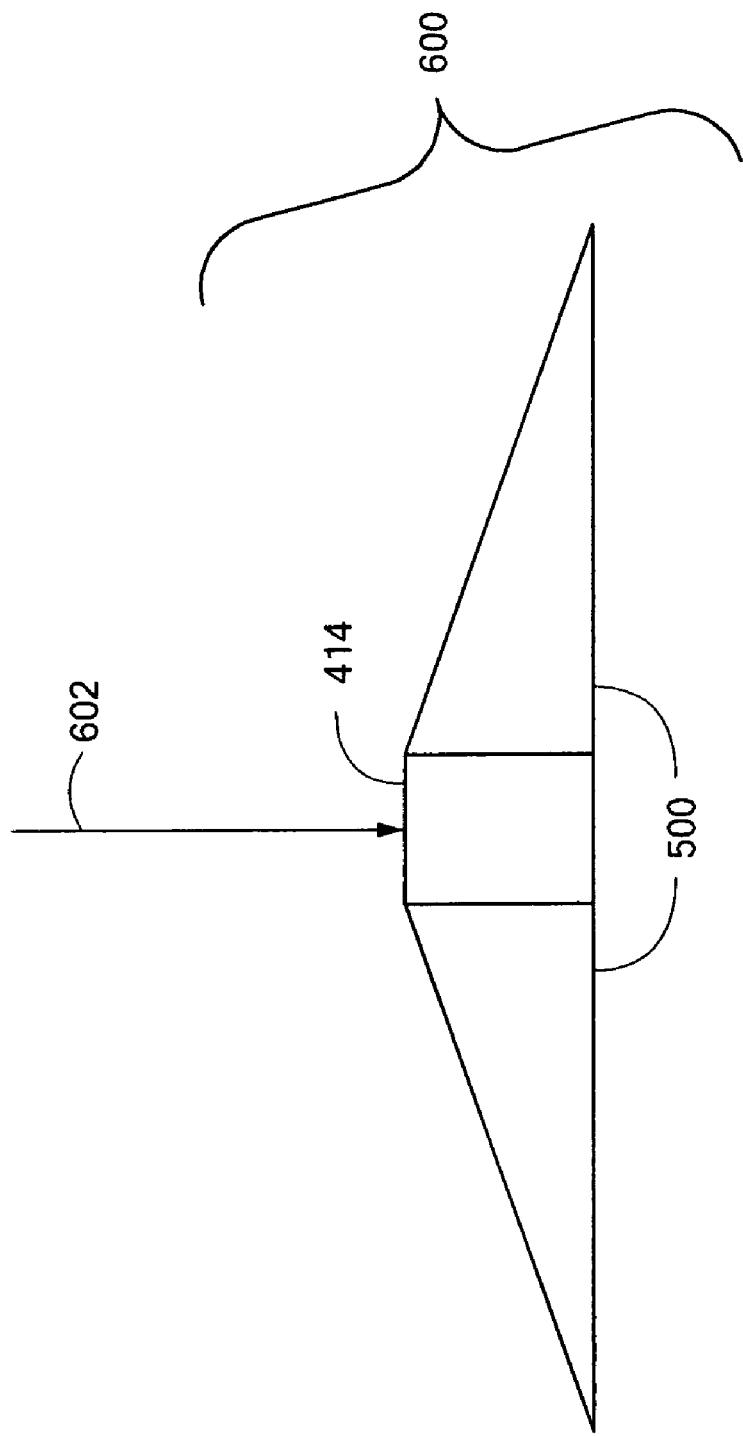
FIG. 6 shows incorporation of a horizontal section of a transmission detector and forward scatter detectors into a rapidly deployable "speed-bump" according to one embodiment of the present invention.

A method for integrating the horizontal section of the transmission detector 414 and the forward scatter detectors 500 into a rapidly deployable module is shown in FIG. 6. The detectors have been integrated into a re-locatable "speed bump" 600 which can be conveniently stored inside the back of the Mobile Inspection Van and which is placed on the roadway prior to commencing scanning vehicles. If necessary, the speed bump can be conveniently broken down into three smaller modules for storage and ease of handling. The vertical leg of the transmission detector would be a separate unit set up on the far side of the vehicle being scanned. X-ray beam axis 602 is shown.

It should be noted that all the claims made in this disclosure are applicable not only to the Mobile Inspection Van as in the earlier referenced patent application, but also to any application of radiation backscatter technology, such as in a ruggedized shipping container that contains similar subsystems as a Mobile Inspection Van.

Bi-Static Compton Scatter Imaging

Equipment and methods are presented here to extend the useful range of Compton scatter imaging systems by separating the location of the x-ray detectors from the x-ray source. In each application the detectors are closer to the subject than the rest of the imaging system, allowing for more scattered flux to be collected than if the detectors were co-located with the x-ray source and other equipment. The arrangement of source, target, and detector is analogous to many applications of bi-static radar.

Because a number of factors figure in the ability to form images from a distance, extending the useful range of a backscatter imaging system may provide one or more of the following advantages: better image quality for a given distance, larger field of view for a given image quality at a given distance, shorter scan time to produce a given image quality at a given distance, and reduced dose to target for a given image quality at a given distance. Long range imaging systems have a variety of security applications. Reduced dose imaging systems are particularly important for the inspection of people.

Figure 7:
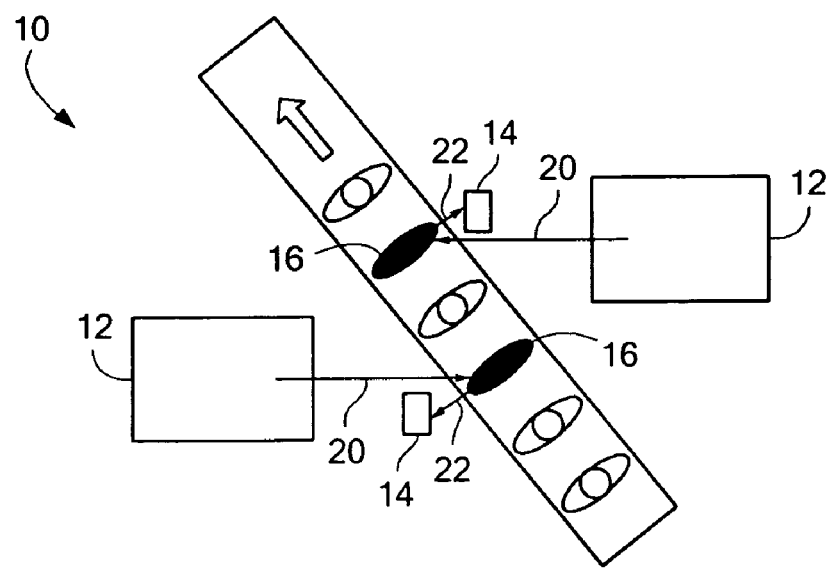
FIG. 7 shows an inspection system designed to inspect personnel.

An inspection system in accordance with preferred embodiments of the present invention is now described with reference to FIG. 7. A source 12 of penetrating radiation directs a beam 20 of penetrating radiation at object 16. Source 12 of penetrating radiation is disposed, with respect to object 16, such that the inspected field of view is less than 0.1 steradians (sr). Object 16 scatters flux 22 which is detected by detector 14. Detector 14 is disposed, with respect to the object, such as to subtend greater than 0.5 steradians in the field of view of the object.

Application to Inspection of Walls for Foreign Objects

In one embodiment of the present invention, described with reference to FIG. 8, the inspection system is configured to rapidly inspect walls for unwanted objects, or perform a variety of non-destructive testing applications such as looking for flaws hidden under the body panels of automobiles.

Figure 8:
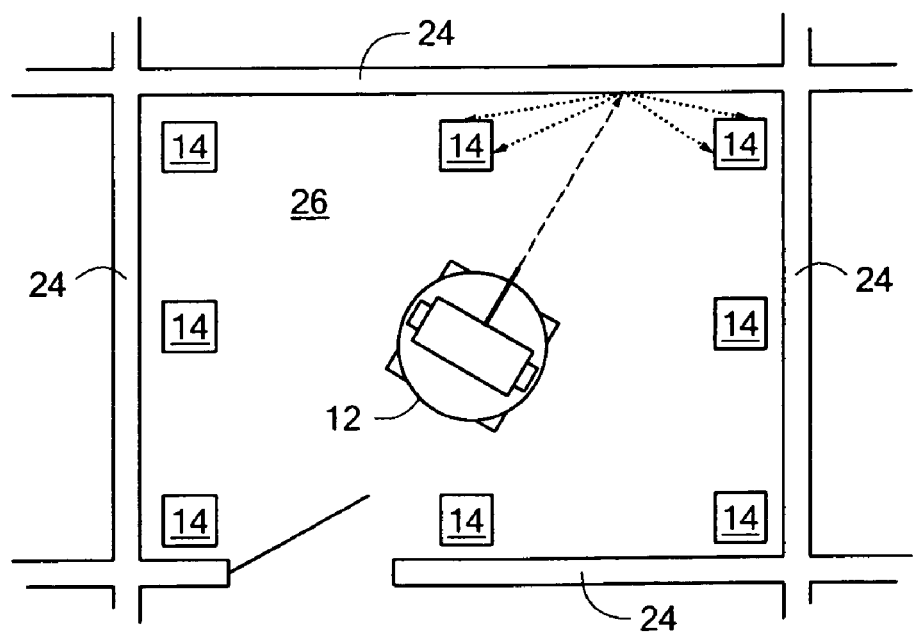
FIG. 8 shows an inspection system designed to inspect walls of a building for foreign objects.

FIG. 8 shows a configuration where source 12 is moved to the center of room 26, from which source 12 can rapidly scan walls 24 of room 26 with penetrating radiation. Detectors 14 are placed near to walls 24. In this configuration, the system can image all of the sections of walls 24 that are not covered by detectors 14. The positions of detectors 14 can then be shifted to allow the inspection system to scan the remaining areas. If source 12 is not displaced when detectors 14 are moved, then both images can be stitched together in software to provide a modest quality image of room 26.

Regions that are found interesting can be scanned more closely using traditional methods whereby both source 12 and detector 14 are placed as close as possible to the area under inspection.

Application to Locate People in Rooms From Adjacent Rooms

Figure 9:
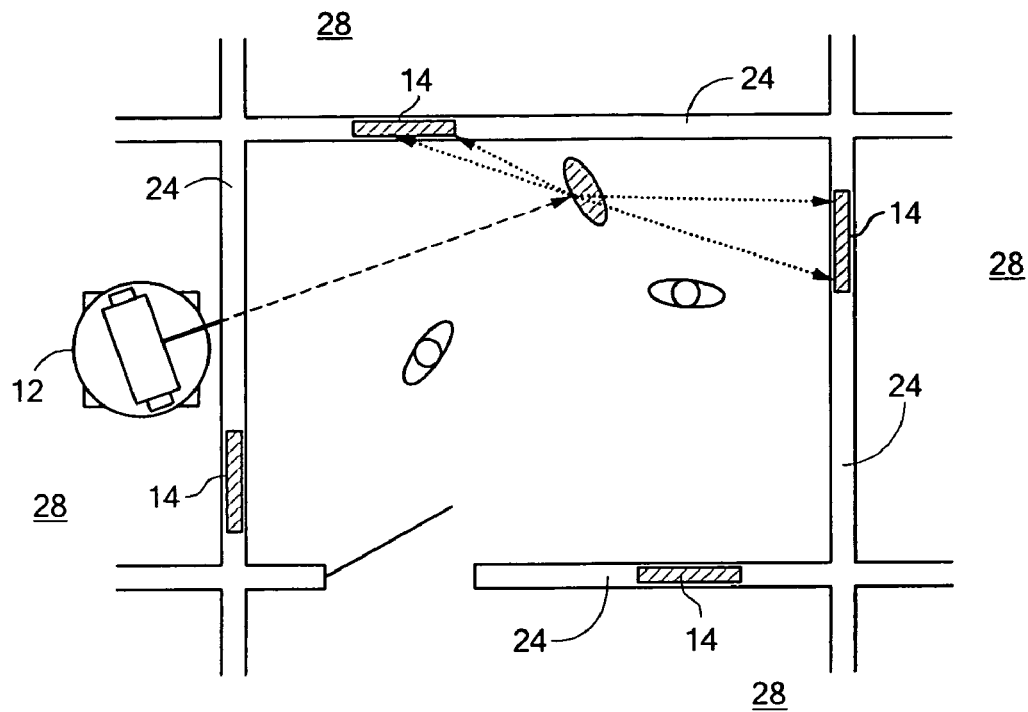
FIG. 9 shows an inspection system designed to located people in an adjacent room with detectors built into the walls of the room.
Figure 10:
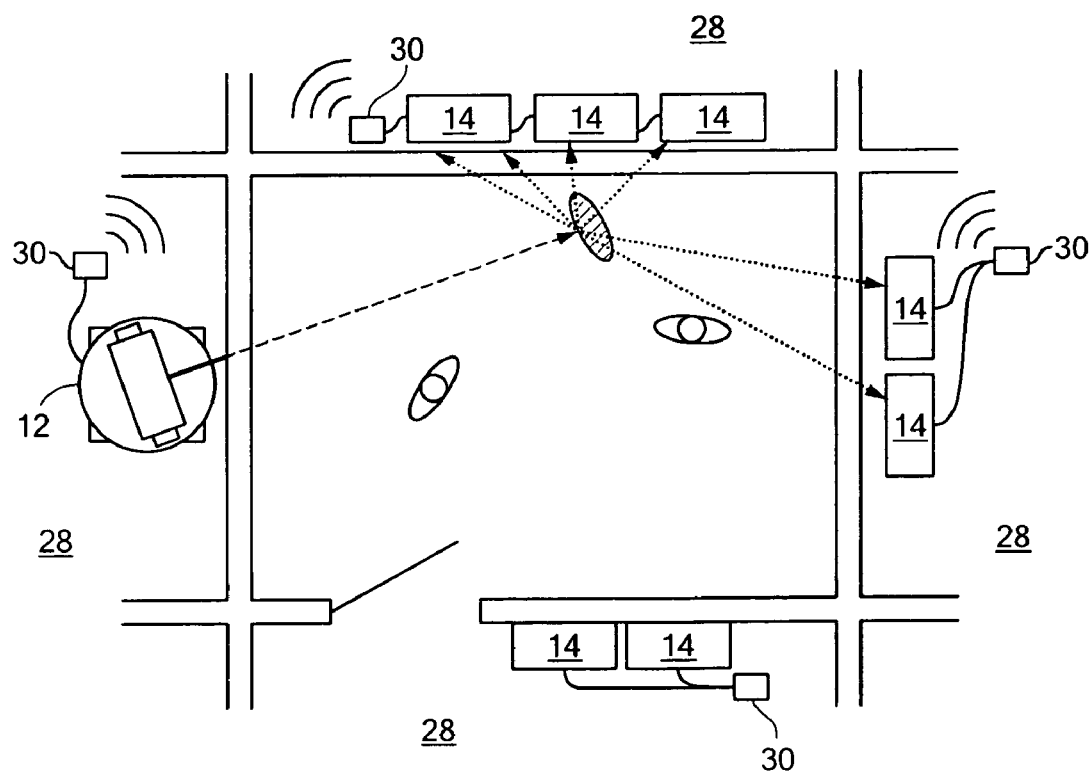
FIG. 10 shows an inspection system designed to locate people in an adjacent room with detectors located in rooms adjacent to the room of interest.

In another embodiment of the present invention, shown in FIG. 9, source 12 is located in an adjacent room 28 and detectors 14 may either be built into walls 24, as shown in FIG. 9, or located in adjacent rooms 28, as shown in FIG. 10. Concealment of detectors may be advantageous in particular applications. Wireless transmitters 30 can be used to connect detectors 14 to a data processing apparatus 32 co-located with X-ray source 12.

In such a configuration, operators are able to first produce a low-dose/low-quality scan that might provide enough information to separate perpetrators from victims. Then, if needed, higher quality higher-dose images could be produced of the perpetrators. In this way, high dose could be limited to a hostage taker while minimizing dose to innocent hostages.

Application to Extend Rage of Existing Inspection Systems

Figure 11:
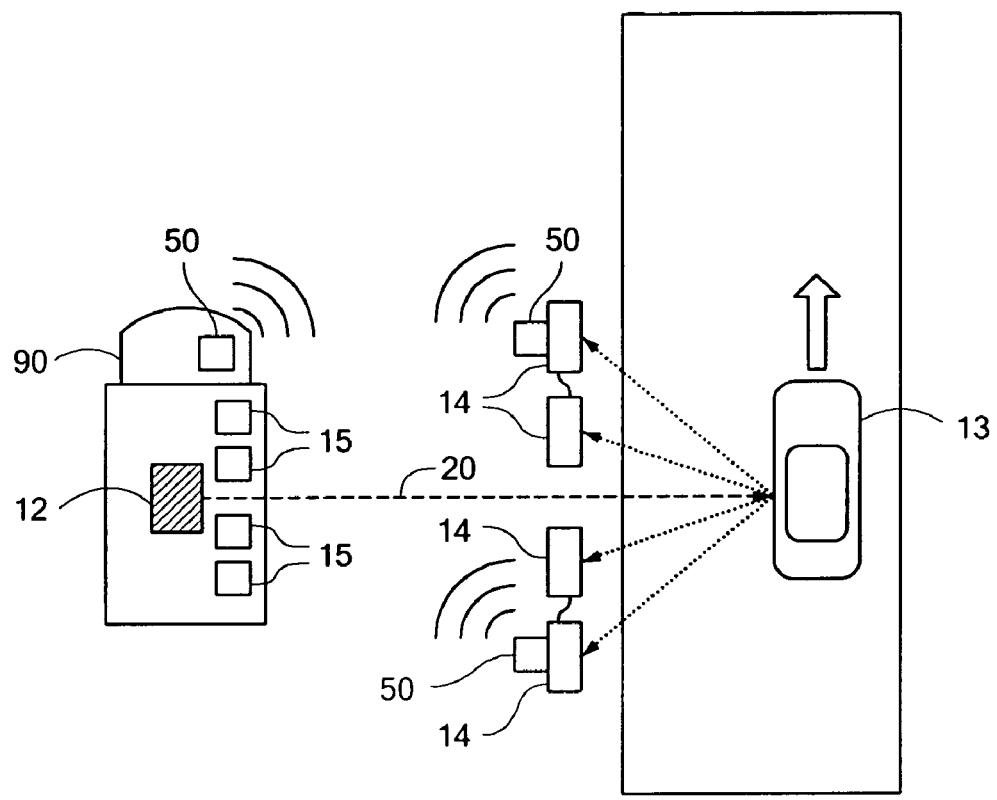
FIG. 11 shows an inspection system designed to extend the range of existing inspection systems by relocating detectors closer to the object being inspection.

As shown in FIG. 11, AS&E presently builds a backscatter imaging product known as the Z-Backscatter Van™ (ZBV™), described, for example, in U.S. Pat. No. 7,099,434. The ZBV, designated generally by numeral 90, is optimized for a target distance of 2-5 feet. ZBV 90 is often deployed in "portal mode", meaning that the ZBV, with X-ray source 12 and detectors 15, is stationary, while target 13 (typically vehicles) drive through the scanning x-ray beam 20.

In the portal operating mode, the range of the ZBV 90 is extended by deploying additional detectors 14 nearer to target 13, as shown in FIG. 11. Such a configuration may have the following advantages over reliance on ZBV's on-board backscatter detector array 15:

In the event of a detonation of the target, only auxiliary detectors 14 would be destroyed.

An arbitrary number of detectors 14 could be deployed, allowing users in the field to trade cost for added image quality when and where needed.

Positions of detectors 14 can be rearranged by the user to vary shadowing; to emphasize data from side scatter or forward scatter; or even to produce transmission x-ray images.

Detectors 14 can transmit data to ZBV 90 electronics by using wireless transmitters 50. The only power needed by detectors 14 is direct current provided by power supplies for the photomultiplier tubes, which may be powered by batteries, and power for the wireless transmitters 50. Alternately, power and signal cables may be used to connect ZBV 90 to detectors 14.

Figure 12:
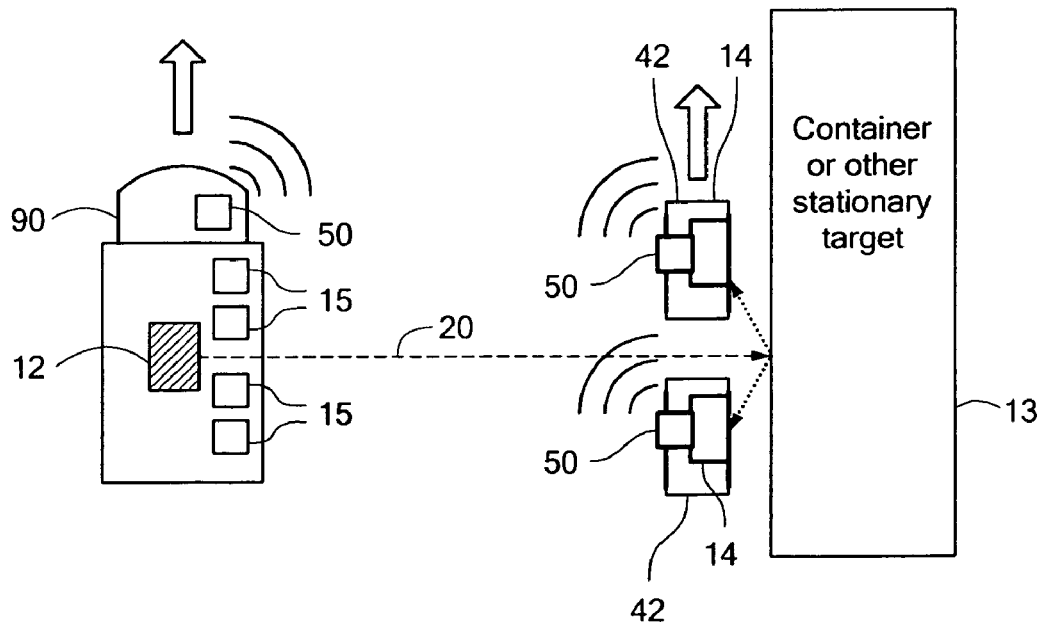
FIG. 12 shows an inspection system with the source of penetrating radiation and detectors located on vehicles capable of road travel.

Detectors 14 are one of the lighter components of the overall x-ray system. A small number of auxiliary detectors can fit into the coach of ZBV 90. A larger supply of detectors can be towed in a small trailer (not shown) behind ZBV 90, or transported in other support vehicles (not shown). As shown in FIG. 12, in order to operate ZBV 90 in drive-by mode (where ZBV 90 drives past target 13 in order to scan X-ray beam 20 over target 13), auxiliary detectors 14 are mounted on robotic drone vehicles 42. In this scenario a wireless link is used to transmit instructions to robotic drone vehicles 42, and to receive data from detectors 14.

Figure 13:
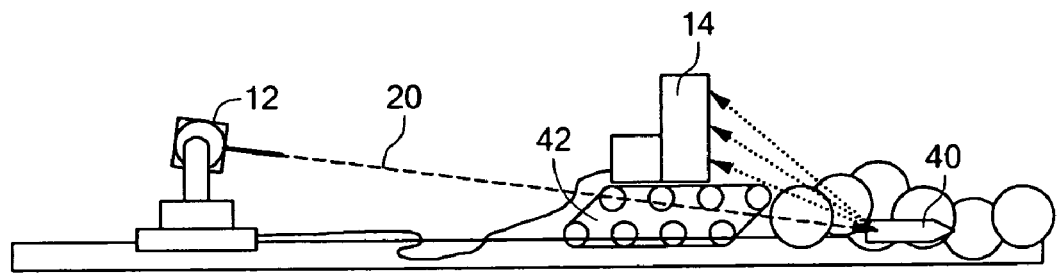
FIG. 13 shows an inspection system designed to inspect possible IEDs with the detector located on a forward deployed robot.

Application Using Forward Deployed Mobile Detectors to Inspect Possible IEDs or Left-Behind Packages An inspection system for detecting possible improvised explosive devices (IEDs), in accordance with the present invention, is now described with reference to FIG. 13. Detector 14 is mounted on small robotic drone vehicle 42. Small robotic drone vehicle 42 brings detector 14 close to IED 40 while x-ray source 12 remains at a safe distance with the operator (not shown). Although robotic drone vehicle 42 is a relatively high cost component compared to a backscatter x-ray system, small robotic drone vehicles 42 designed for military applications have often survived explosions, and robotic drone vehicle 42 could be further protected with blast armor.

The location of detector 14 with respect to IED 40 causes different shadowing effects in the resulting image. If detector 14 is placed on only one side of primary x-ray beam 44, the image will have shadows analogous to what one would see in a photograph with the camera at the position of x-ray source 12 and with a light source at the location of x-ray detector 14. These shadows often prove useful in interpreting images, as they give objects a three dimensional appearance and make certain edges more apparent. More edges can be enhanced by moving detector 14 to a new location, or using several detectors simultaneously with data from each detector 14 processed separately. Experiments at AS&E have shown that the effect can be even more useful when images from several detectors at two or more angles are mixed in different ratios.

Two or more detectors 14 on two or more robots 42 can be used to fully exploit this detector mixing concept. Alternately, after a single image is produced using a single detector 14, detector 14 can be moved to a new location while x-ray source 12 does not move, and then a second image is produced. These sequential images could be combined (to increase the effective flux) and mixed in different ratios to exploit different possible shadow configurations.

Application Using Forward Deployed Mobile Detectors to Scan a Roadside for IEDs

Figure 14:
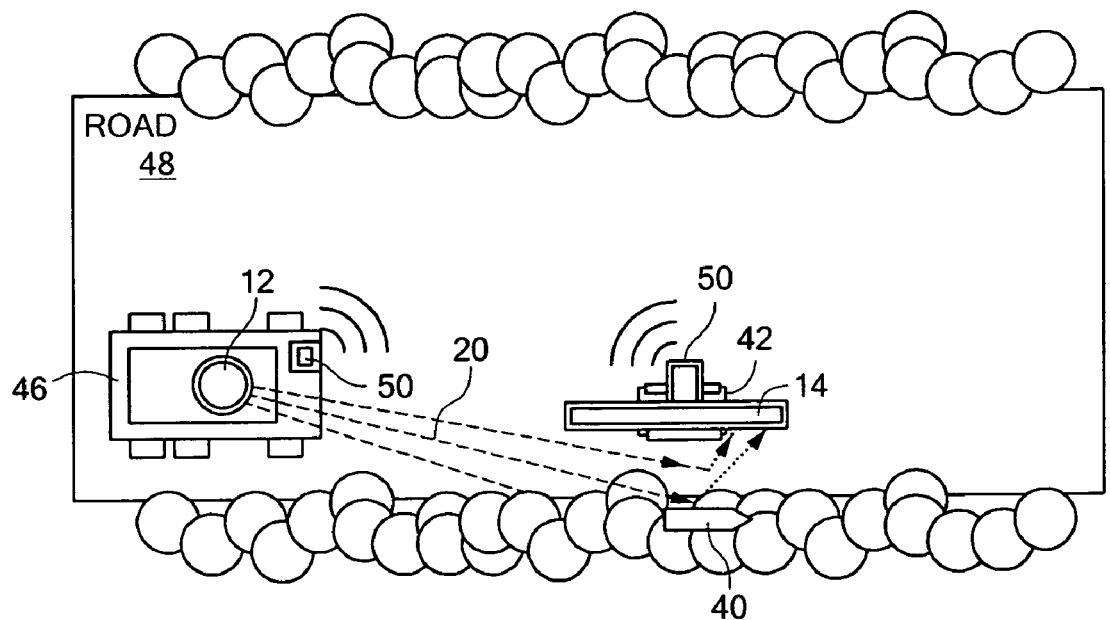
FIG. 14 shows a top view of an inspection system with the source of penetrating radiation mounted to a swivel mount on a vehicle capable of road travel and the detector mounted on a drone vehicle.

A fully mobile variant of the previous embodiment is capable of 'sweeping' for roadside IEDs, as shown in FIG. 14. X-ray source 12 is mounted on vehicle 46. Vehicle 46 may or may not be armored. A beam chopper wheel (not shown) scand beam 20 in a direction perpendicular to road 48 while vehicle 46 drives slowly in the direction of road 48, in order to produce a 2-D image. Detector 14 would drive ahead of vehicle 46 on a small robotic drone vehicle 42. If cable management between the vehicle 46 and robotic drone vehicle 42 poses a problem, then cabling can be replaced by wireless communication system 50 to direct robotic drone vehicle 42 and receive signals from detector 14.

Figure 15:
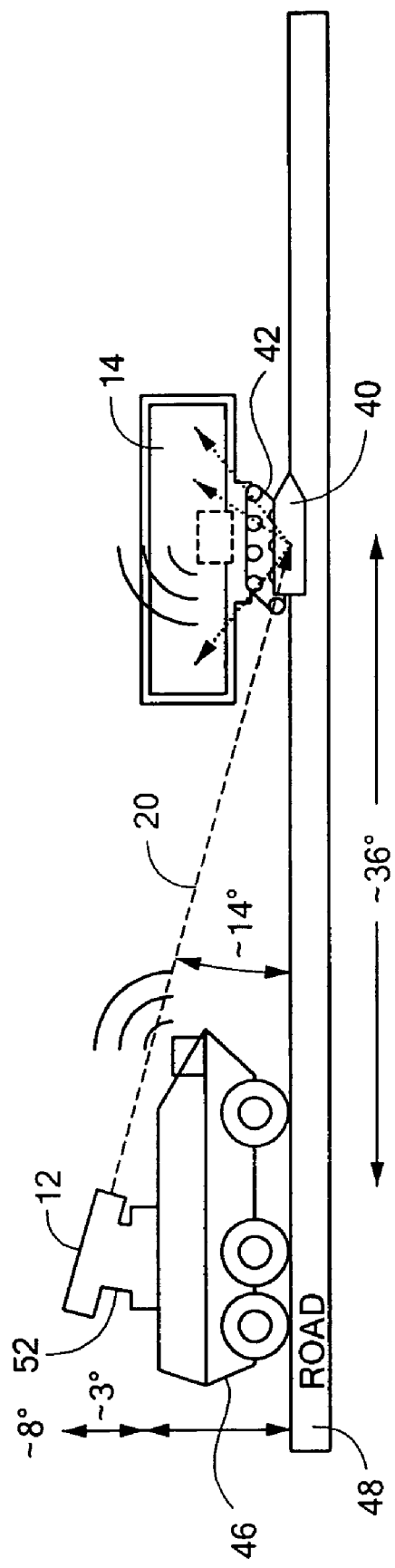
FIG. 15 shows a side view of an inspection system with the source of penetrating radiation mounted to a swivel mount on a vehicle capable of road travel and the detector mounted on a drone vehicle.

As depicted in FIG. 15, x-ray source 12 may be attached to swivel mount 52, so that either side of road 48 can be imaged, or object 40 lying in road 48 can be inspected.

Variations in the speed of vehicle 46 can cause distortions in the image. These variations typically do not inhibit the interpretations of backscatter images, however, the distortions might be more problematic in long-range applications. A scan drive might be employed to regulate the speed of both vehicle 46 carrying x-ray source 12, and robotic drone vehicle 42 carrying detector 14.

A greater challenge is posed by uneven road surfaces and bumps in the road. These cause x-ray source 12 to bounce up and down, producing corresponding distortions in the image. Although these distortions are usually not a problem for scans at a distance of a few feet, their effect will grow in proportion to the distance. A change in the attitude of the vehicle of one degree, for example, will move beam 20 only 1" at a distance of 5 feet. However, beam 20 will be displaced by 6" at a distance of 30 feet. A given distortion will be even more apparent (relative to existing systems) because long range systems such as the present invention will typically work with much smaller fields of view than have been used on short range systems.

In accordance with various embodiments of the invention, x-ray source 12 is stabilized using the same technologies that are used to stabilize the cannon on a modern tank. Since the chopper wheel (not shown) itself is large gyroscope, the chopper wheel may be mounted on a suspension of gimbals and shock absorbers to minimize changes in attitude of x-ray beam 20 while vehicle 46 moves over uneven terrain.

The image is much less sensitive to changes in the position of detector 14. Changes in attitude or elevation of detector 14 during a scan would cause only small changes in the shadowing of the image, which would not interfere with interpretation of the image, and would likely not even be noticed.

Application for Surveillance of Select Vehicles or Persons Traversing a Defined Passageway In another embodiment of the bi-static backscatter concept, persons or vehicles subject to inspection might be directed to traverse a well defined region. This region might be a walkway in an airport or a roadway or tunnel through which vehicles pass.

Existing concepts for inspecting every person in such a situation require space for a complete backscatter source and detector adjacent to the through-way. Moreover, subjects must pass through the beam at a specified speed, subjects are only inspected from the sid, and every subject passing through the inspection area must be irradiated.

Figure 16:
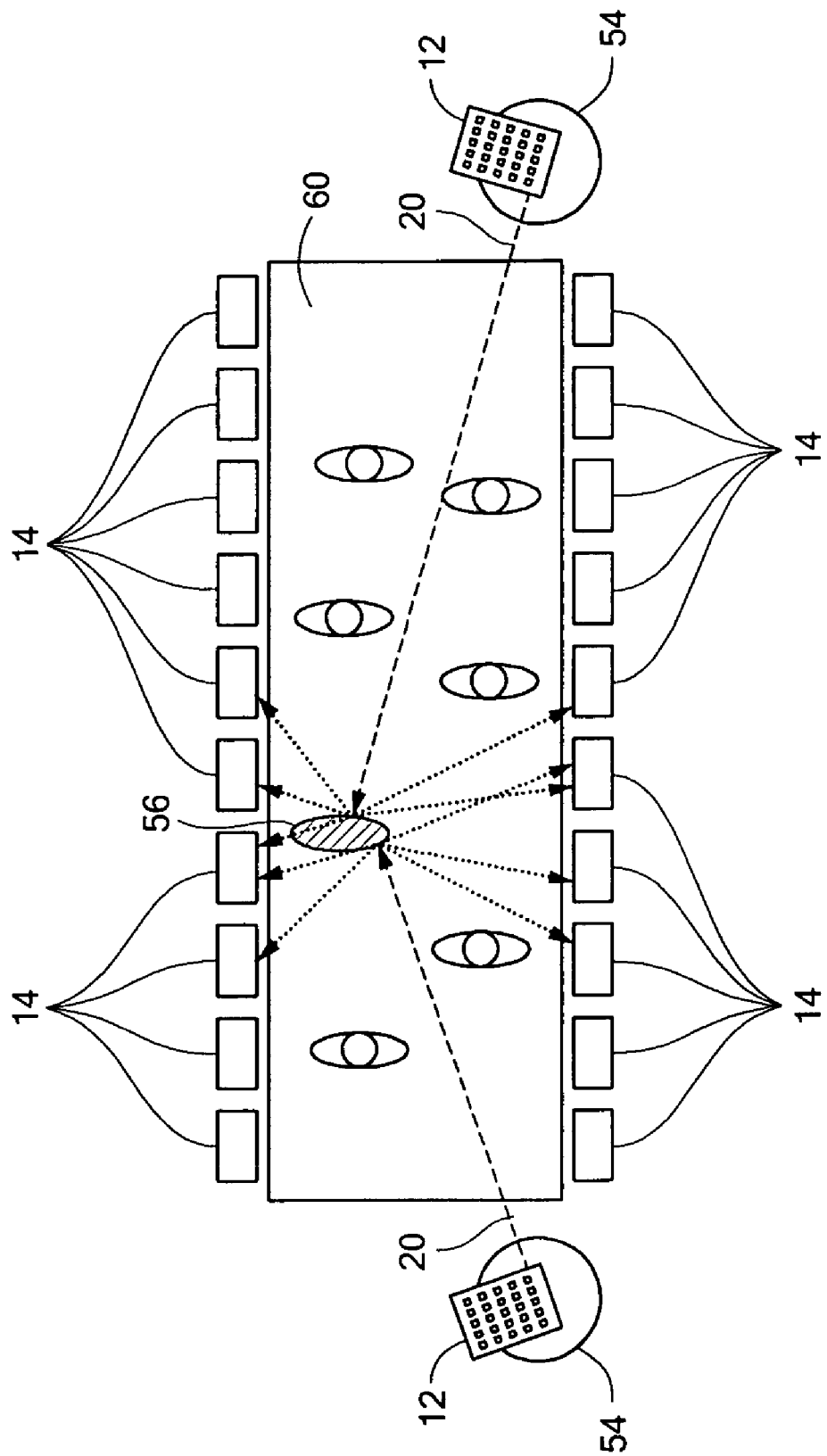
FIG. 16 shows an inspection system for inspecting suspect travelers with the x-ray source mounted in the ceiling.
Figure 17:
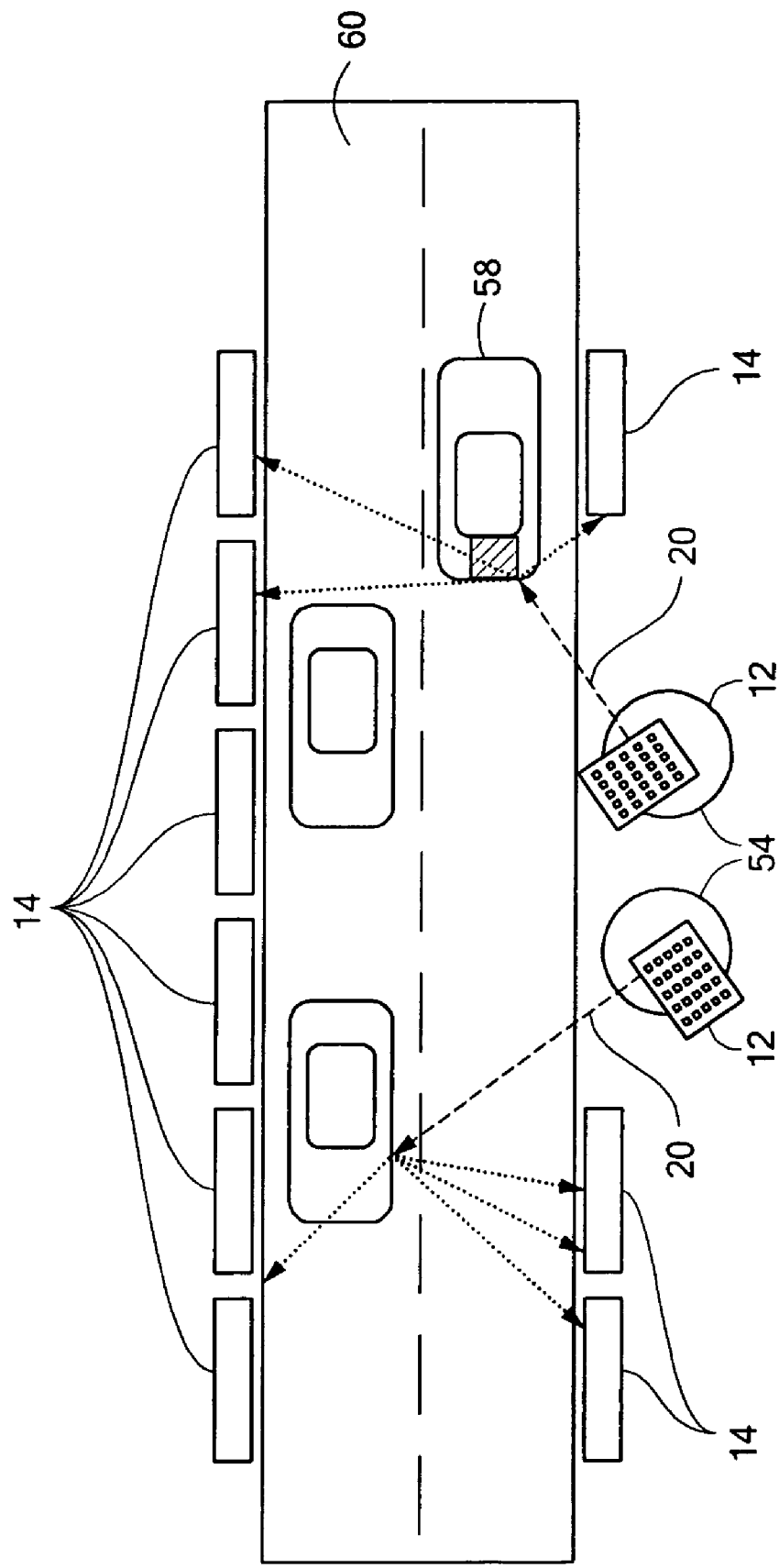
FIG. 17 shows an inspection system for inspecting passing cars with the detectors located along the roadway and the x-ray source mounted above the roadway.

Situations where any one of the above constraints is unacceptable can be addressed by a configuration such as is shown in FIGS. 16 and 17. X-ray sources 12 are attached to pivoting mount 54 aimed to select any arbitrary subset of a larger region for scanning with x-ray beam 20.

In each of these systems, operators select person 56 (in FIG. 16), or vehicle 58 (in FIG. 17), and paint only that target with X-rays. Person 56, or vehicle 58, can be studied for as long as it is within passageway 60 which is lined with detectors 14.

If passageway 60 is a narrow hallway, (or if the roadway passes through a tunnel) then detectors 14 can easily be concealed in walls and/or ceiling or disguised as part of the walls or ceiling. In some circumstances it might also be feasible to build detectors 14 into the surface of passageway 60. In a configuration where detectors 14 are deployed in the walls, floor, and ceiling of a tunnel, it is possible to achieve coverage of nearly $4\pi$ sr, thereby making use of the greatest possible fraction of scattered photons. Such a system achieves far higher collection efficiency of scattered photons than current near-field, Compton scatter imaging systems.

Figure 18:
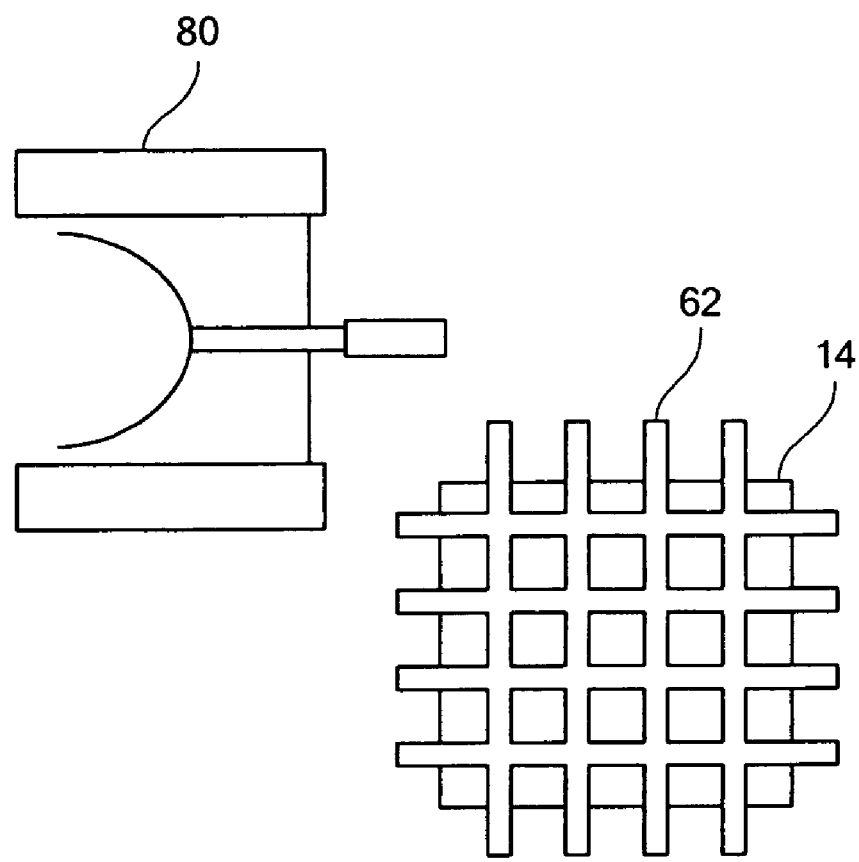
FIG. 18 shows a top view of the detector located in the ground with structural support.

As shown in FIG. 16, x-ray sources 12 may be located in the ceiling so operators are better able to steer around uninteresting people. In FIG. 18, x-ray sources 12 are drawn at the side of passageway 60. However, in a tunnel, X-ray sources 12 may also be suspended from the ceiling.

The use of multiple X-ray sources 12, or even a single x-ray source 12 which can be aimed from the middle towards both ends of passageway 60, allows operators to image person 56 or vehicle 58 from multiple angles. If multiple X-ray sources 12 are aimed at the same object, or objects that are near to one another, then the X-ray sources 12 need to be electronically synchronized so that at any instant, only one is shooting.

Encoders on the source-aiming mechanics may be used to identify target location(s) and only allow signal from nearest detectors to be processed, in order to limit electronic noise and air scatter.

By imaging person 56 or vehicle 58 from a distance, speed becomes a less critical factor than in near field imaging systems, because angular speed is much smaller when viewed from a distance. Imaging the target from an angle that is nearly in line with the target's direction of motion further reduces apparent angular movement and further facilitates the imaging of a moving object.

Figure 19:
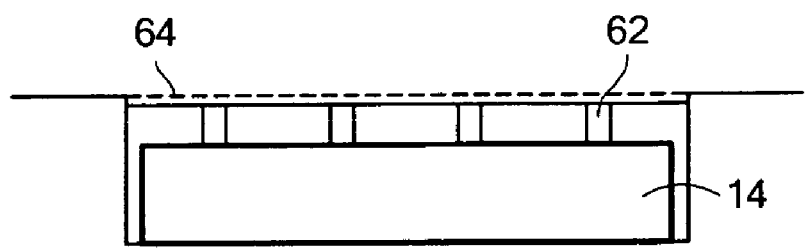
FIG. 19 shows a side view of the detector located in the ground with structural supports and camouflage layer.

Detectors 14 built into the floor or road surface, as shown in FIGS. 18 and 19, must be able to support the weight of any object 80 (people, animals, or vehicles) that might move over them. Strong solid supports such as steel plates are typically not used on the fronts of Compton scatter detectors because the energy of the Compton scattered x-rays is typically too low to penetrate such structures. However, structural support grid 62 made of a structural material (such as steel) can be placed over detector 14, as is shown FIGS. 18 and 19. The detection efficiency of detector 14 will only be reduced by that fraction of detector area which is blocked by solid parts of structural support grid 62. The structural support grid 62 will not produce artifacts of any kind in Compton scatter images, because Compton scatter x-ray images are spatially modulated by the movement of the primary x-ray beam, rather than by pixilation of the detectors 14, as is the case in most transmission x-ray and optical imaging systems.

Detector 14 may be concealed, by camouflage 64, or otherwise, in some cases, at the further expense of attenuating the x-ray signal. In outdoor applications, a thin layer of dirt or leaves might be used. In an airport walkway a thin sheet of plastic with decorative patterns could obscure any identifying features of detector 14.

Application for Broad Area Surveillance

Figure 20:
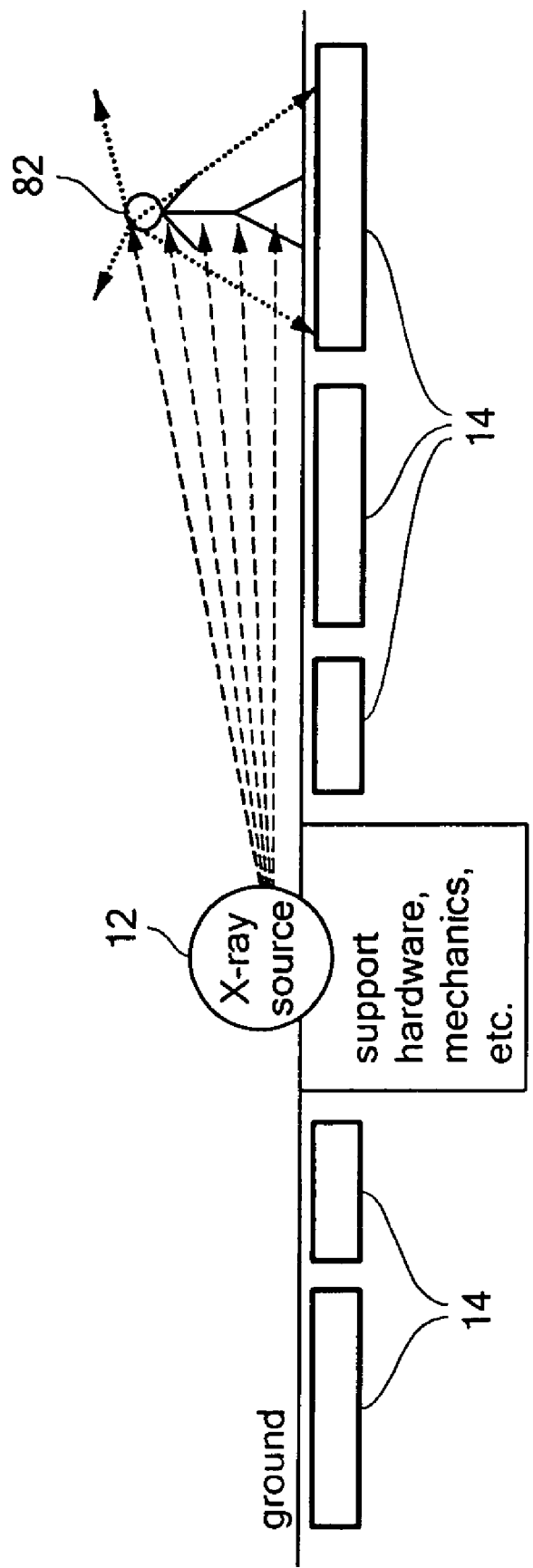
FIG. 20 shows a side view of an inspection system with an array of detectors, located in the ground, surrounding the x-ray source.
Figure 21:
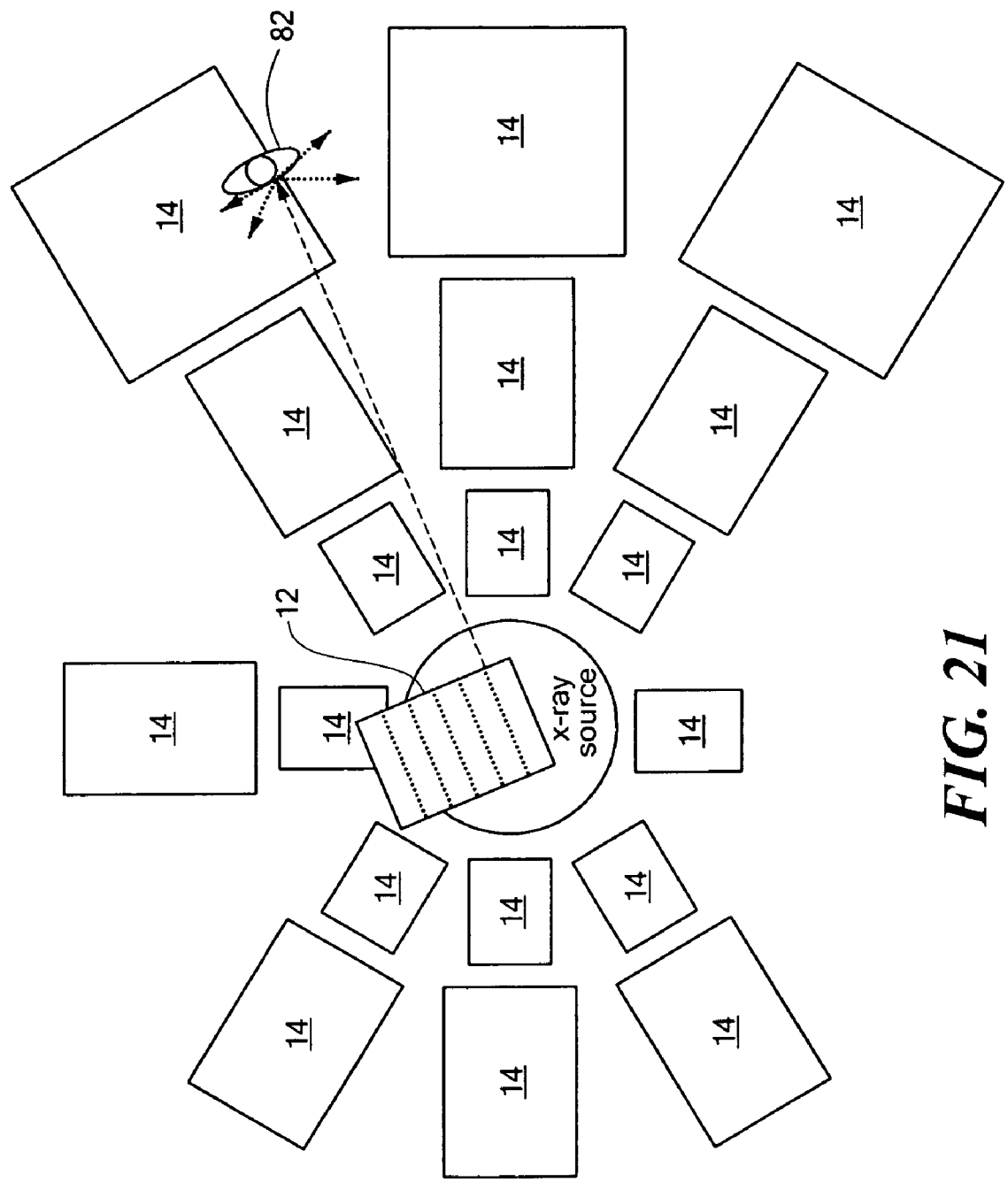
FIG. 21 shows a top view of an inspection system with an array of detectors, located in the ground, surrounding the x-ray source.

In another embodiment, shown in FIGS. 20 and 21, an array of detectors 14 is located in regions of interest, and the entire region may be "painted" by single x-ray source 12.

Detectors 14 are arrayed in or on the ground in the region for surveillance. X-ray source 12 is in a central location, able to "shoot" at all regions where detectors 14 are located. This way X-ray flux used for imaging each pixel of a given target is roughly independent of distance, because no matter where in the region object 82 stands, object 82 is still roughly the same distance from the nearest detectors 14. X-ray source 12 might scan azimuthally through as much as 360 degrees, in a manner similar to a radar system.

In this continuous sweep mode, once the scan area is surveyed, the backscatter signal at any point should not change unless a new object were introduced. Therefore, a computer could monitor the image, or just the integrated signal from any given region in the image, and alert human operators in the event of a change. A sudden increase in image density might indicate the presence of a living intruder (person or animal). More subtle changes might indicate motion of objects (e.g. vehicles entering the region, or movement of camouflaged people/vehicles that have been hiding in the region since before the scan started). Alternately, an optical or infrared imaging system might be used in a similar way to automatically detect potential threats. Once a potential threat is flagged, the system could automatically begin a more detailed Compton x-ray scan to produce an image to be analyzed by a human operator.

Pressure sensors (not shown) might be integrated with detectors 14 in the ground. In this case, the pressure sensors would be the first detection system. Then a computer might automatically aim the X-ray beam 20 at the region in question and produce an image.

A continuous sweep mode might also be used to scan a crowd for potential suicide bombers.

Pressure sensors integrated with detectors 14 and placed in the ground around detectors 14 may be used to sense when object 82 is moving in parallel with the path of the beam. This information can be used by an automatic safety system to limit the dose to object 82 by shutting off beam 20 or changing the sweep path. The best solid angle coverage is achieved with a tiled pattern of detectors 14 'carpeting' the ground.

In certain embodiments of the invention, detectors 14 may be camouflaged by thin layer of dirt, or otherwise concealed, although some forms of camouflage may result in a reduction in signal. Alternatively, or additionally, detectors 14 may also be hidden in above-ground objects such as artificial rocks or trees, although a large solid angle coverage would be unlikely in this case.

Figure 22:
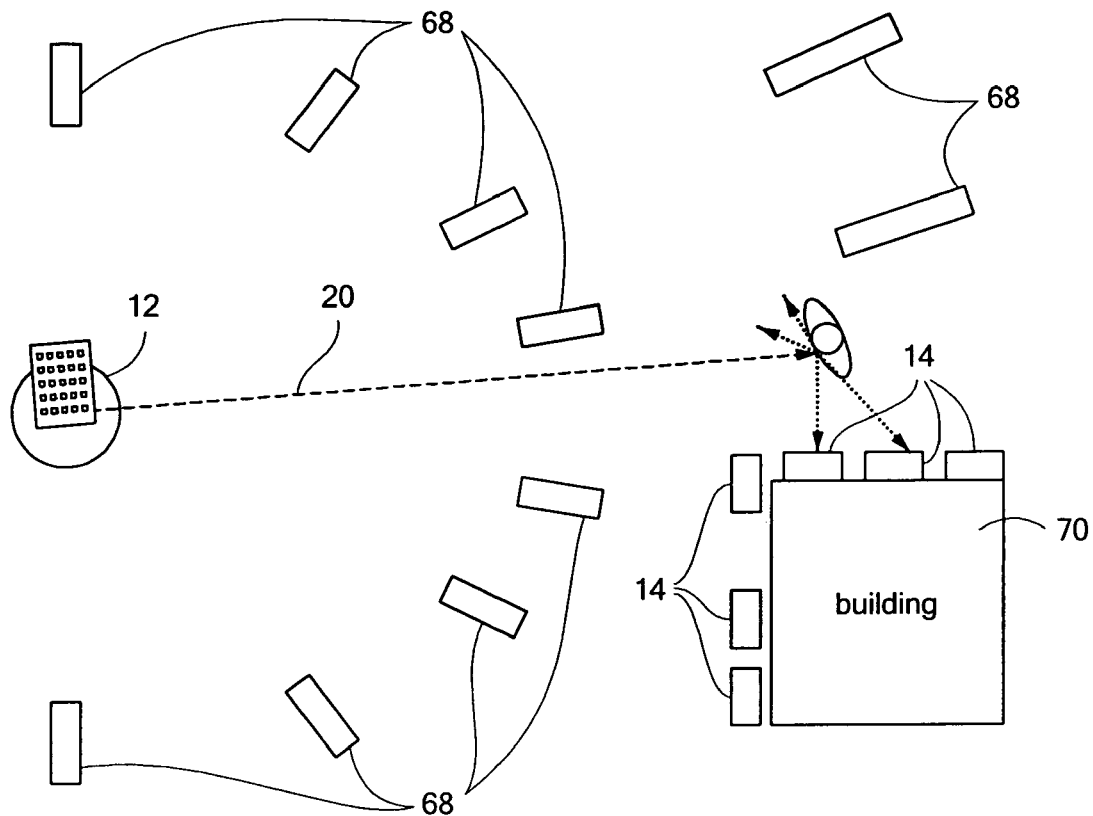
FIG. 22 shows a top view of an inspection system where the detectors are free standing monoliths.

Detectors 14 may be deployed as free standing monoliths 68, as shown in FIG. 22, though a large solid angle would require filling much of the area with monoliths 68, which might obstruct visual lines of sight from x-ray source 12 to potential targets of interest. Building 70 and other sensitive structures might have detectors 14 mounted on the building walls.

Electronic noise could be limited by only processing signals from those detectors 14 that are near the target of the x-ray beam 20.

If the beam 20 is fired directly towards a detector 14, that signal is processed separately, as it would be predominantly a transmission image signal rather than a Compton scatter signal. Encoders on the source positioning device could indicate the position of the x-ray beam spot in order to indicate to the control system when detector 14 is in the direct path of beam 20.

The electronics and software are designed to allow the user to deploy and configure any number of detectors 14 in any chosen configuration. Different terrain and different applications would require different configurations and numbers of detectors 14.

Figure 23:
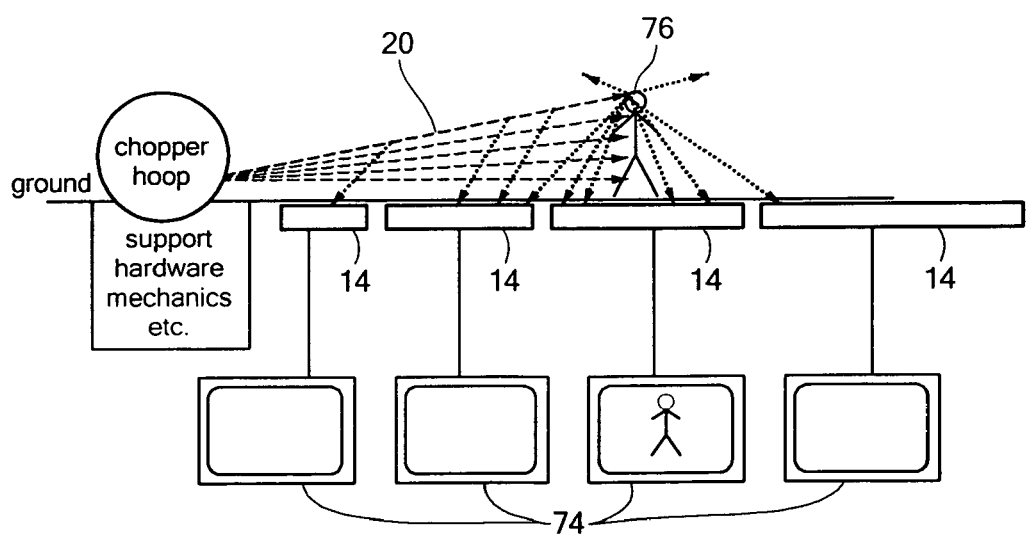
FIG. 23 shows an inspection system in which the signals from detectors at different distances are separated.

Air scatter becomes a more important consideration when scanning at a distance. Detectors 14 near to the primary beam 20 receive an air scatter signal which will 'fog' the image. The noise caused by this effect might be mitigated by reading the signals from detectors 14 at different distances in separate channels 74, as is shown in FIG. 23, so that person 76 is imaged in only one detector, and that image contains only the air scatter background from that detector (or the set of detectors in that region). Detectors 14 located along the path of the primary beam 20 which are not near to the target receive much less signal from the target and therefore have a much higher ratio of noise to signal. The overall signal-to-noise ratio would be improved by ignoring the entire signal from these detectors.

Although various exemplary embodiments of the invention have been disclosed, it should be apparent to those skilled in the art that various changes and modifications can be made which will achieve some of the advantages of the invention without departing from the true scope of the invention.

What is claimed is:

1. An inspection system for inspecting an object, the system comprising:
   a source of penetrating radiation, disposed with respect to the object such that the inspected field of view is less than 0.1 steradians;
   a spatial modulator for forming the penetrating radiation into a beam for irradiating an object with a scanning profile;
   a detector for detecting scattered radiation from the object, separated from the source of penetrating radiation, and disposed, with respect to the object, such as to subtend greater than 0.5 steradians in a field of view of the object.

2. An inspection system according to claim 1, wherein the source of penetrating radiation and the detector are located on vehicles capable of road travel.

3. An inspection system according to claim 2, wherein the vehicles are robotic drone vehicles.

4. An inspection system according to claim 2 or 3, further comprising: a scan drive configured to regulate the speed of the vehicles.

5. An inspection system according to claim 2, wherein the detectors are buried in the ground in the area of interest.

6. An inspection system according to claim 5 further comprising: a structural support grid to protect the detectors from a passing object.

7. An inspection system according to claim 5 further comprising: pressure sensors integrated with the detectors configured to detect the presence of an object.

8. An inspection system according to claim 1, wherein the detectors are built into the walls of a room.

9. An inspection system according to claim 1, wherein the detectors are easily relocatable by hand.

10. An inspection system according to claim 1, wherein the source of radiation is an X-ray tube.

11. An inspection system according to claim 1, wherein the source of radiation is a gamma ray beam.

12. An inspection system according to claim 1, further comprising one or more chopper wheels with apertures configured to scan past the source and generate a scanning pencil beam.

13. An inspection system according to claim 1, further comprising a computer configured to continuously monitor output from repeat scans of the same region and automatically detect change.

14. An inspection system according to claim 1, wherein the source of penetrating radiation is mounted on a pivot mount.

15. An inspection system according to claim 1 further comprising: a stabilizer system configured to minimize source bounce on rough terrain.

16. An inspection system according to claim 1, wherein the detectors are concealed.

17. An inspection system according to claim 16, wherein the detectors are concealed in a ceiling.

18. The inspection system according to claim 1, wherein the detectors are free standing monoliths.

* * * * *